United States Patent [19]
Nicholson

[11] Patent Number: 6,131,577
[45] Date of Patent: *Oct. 17, 2000

[54] SELECTIVE ENHANCEMENT OF HYPERTHERMIA IN RF AND MICROWAVE IRRADIATION OF DISEASED OR EXCESS TISSUE

[76] Inventor: James E. Nicholson, 14 Meadowdam Rd., Lincoln, Mass. 01773

[ * ] Notice: This patent issued on a continued prosecution application filed under 37 CFR 1.53(d), and is subject to the twenty year patent term provisions of 35 U.S.C. 154(a)(2).

[21] Appl. No.: 08/841,273

[22] Filed: Apr. 29, 1997

[51] Int. Cl.$^7$ .................................................. A61B 19/00

[52] U.S. Cl. ............................................ 128/898; 607/101

[58] Field of Search ............................... 607/101, 91–92, 607/100; 128/898; 604/19–21

[56] References Cited

U.S. PATENT DOCUMENTS

| | | | |
|---|---|---|---|
| 5,445,608 | 8/1995 | Chen et al. | 604/20 |
| 5,480,417 | 1/1996 | Hascoet et al. | 607/101 |

*Primary Examiner*—V. Millin
*Assistant Examiner*—Kelly O'Hara
*Attorney, Agent, or Firm*—Williams & Associates; Frederick C. Williams

[57] ABSTRACT

Method and use of injected fluids for enhancement of absorption of radiofrequency and microwave radiation in tissue. Biocompatible fluids or solutions with absorption properties greater than that of the target tissue are injected into the target tissue, which is then irradiated with appropriate frequency radio-frequency or microwave radiation. Absorption produces heat selectively in the target tissue, thereby producing desired ablation of excess or diseased tissue.

20 Claims, 4 Drawing Sheets

SELECTIVE ENHANCEMENT OF HYPERTHERMIA IN RF AND MICROWAVE IRRADIATION OF DISEASED OR EXCESS TISSUE

BACKGROUND OF INVENTION

1. Field of Invention

This invention relates generally to ablation of diseased or excess tissue by delivery of electromagnetic radiation to the target tissue. In this process, the absorption of electromagnetic radiation by various physical mechanisms causes heating sufficient to create necrosis and resorption of the target tissue. The electromagnetic radiation is often but not exclusively delivered by some form of antenna.

2. Background of the Invention

Conventionally "microwave" radiation is the designation for radio energy at frequencies from about 300 Megahertz (MHz) to about 30,000 MHz. In this application, the term "microwave" refers to that frequency range and the term "radio-frequency" (RF) is used to describe electromagnetic radiation at frequencies below that level.

Systems for tissue ablation in diverse circumstances using RF and microwave energy are or will very soon be available commercially. Two such systems for the treatment of prostate enlargement are known.

Benign Prostatic Hyperplasia (BPH), non-malignant tissue growth in the prostate gland anterior to and lateral to the urethra, is the most common affliction of the internal organs in men and is a significant problem for a majority of men over the age of about 50. BPH growth normally begins away from glandular tissue posterior to the urethra, which remains healthy. The benign tumorous tissue growth results in narrowing of the canal through which the urethra passes and consequent pressure on and narrowing of the urethra itself, leading to well known symptoms.

Historically this condition has been relieved by invasive surgery, but the potential side effects of the standard surgery are significant. New treatments for the prostate, however, use selective heating of the diseased prostate tissue to temperatures above 45° C., thereby producing necrosis and resorption. This approach is more likely to avoid damage to the urethra. The principal sources of energy for heating to date include microwaves, RF induction, and RF localized current. See DeFord, Ely, and Fearnot, U.S. Pat. No. 5,304,214, Apr. 19, 1994, "Transurethral Ablation Catheter," Col. 1.

A system for transurethral needle ablation (TUNA®), produced by Vidamed, Inc., uses RF electromagnetic energy at approximately 465 kHz to heat diseased prostate tissue. The TUNA® system conducts 465 kHz current from a needle inserted into prostate tissue via a urethral catheter to a ground. This system raises the temperature of tissue adjacent to the needle above 45° C., the temperature is necessary to cause necrosis and resorption of tissue, by resistive heating and by induction. Issa, M. M. and Oesterling, J. E., "Transurethral needle ablation (TUNA™); an overview of radiofrequency thermal therapy for the treatment of benign prostatic hyperplasia," Current Opinion in Urology 6:20–27 (1996). (Another reference states the TUNA® frequency as 490 kHz. Schulman, C. C. and Zlotta, A. R., "TUNA: A promising new therapy for BPH," Contemporary Urology, October 1995.)

Another system for treatment of BHP, that of Urologix, Inc., applies microwave energy radiated at a frequency of approximately 915 MHz using an impedance matched helical antenna. In this technique, a microwave antenna located within a cannula is inserted into the urethra. When energized, the antenna heats adjacent tissue by induction and molecular excitation, thereby raising the temperature of the target tissue above 45° C. and necrosing the excess prostatic tissue. See, e.g., Rudie, Neilson, and Kauphusman, U.S. Pat. No. 5,326,343, Jul. 5, 1994 (assigned to Urologix, Inc.). For further descriptions of this technique see Mendecki et al., Microwave Applicators . . . . Prostate," Int. J. Radiation Oncology Biol. Phys. vol. 6 No. 11, Nov. 1980, pp 1583–1588; Tadashi Harada et al., "Microwave Surgical Treatment of Diseases of Prostate," Urology, December 1985, vol. XXVI, No. 6, pp 572–576; Rick McClure, "Transurethral Hyperthermia for BPH: Trials goal is to top 80% success," Medical Tribune, vol. 29 No. 9, Mar. 31, 1988 (Thursday), pp 3, 13–14.

In a different application, another system uses RF energy to ablate excess tissue in the mouth, throat, and nose. This system, being developed by Somnus Medical Technologies, Inc., uses RF energy delivered through needles. (See U.S. Pat. No. 5,456,662.) This system operates very similarly to the TUNA® system described above.

These systems and others like them are showing promise for the tissue ablation tasks for which they are designed. However, various factors limit their usefulness.

Raising the temperature of target tissue sufficient to cause necrosis and resorption requires deposition of significant amounts of RF or microwave energy. In addition, in order to avoid conductive dissipation of the heat generated and collateral damage to adjacent tissue, it is desirable to deposit the microwave energy with a high energy density to produce rapid heating in the target tissue. Given the size limitation for devices, such as antennas or needles, which can be inserted via catheters to deposit RF or microwave energy, it is difficult to generate enough energy density in the target tissue to produce the desired result. Further, needle delivery of conducted RF has the limitation that tissue is destroyed only quite close to the needle. Accordingly, treatments may have to be administered in less than optimal ways or for more than optimal times. It would be desirable to have a means for enhancing the deposition of microwave energy in target tissue while leaving surrounding tissue relatively unaffected.

In addition, the absorption of microwave radiation in tissue is not selective. Radiating microwave energy through the urethra, for example, may cause nearly as much damage to the urethra as to the adjacent prostate tissue. Selectivity in other applications can be a problem as well. Since it is usually desirable to preserve the patient's adjacent non-target tissue as much as possible, this result is less than optimal.

Sievert et al., U. S. Pat. No. 5,197,940, issued Mar. 30, 1993, approached the objective of enhancement using seeding. These inventors first seed the prostate with metallic slivers. The second step is to use an antenna to irradiate the patient with RF radiation at approximately 115 kHz. Sievert et al. recommend frequencies from 50 to 200 kHz and possibly up to 500 kHz. The seeds are tailored to absorb the radiation and heat surrounding tissue. The limitation of this invention is the necessity to emplace the seeds.

It is therefore an object of the current invention to provide an improvement to the method of depositing RF and microwave ablation of tissue, for example for treating prostate hyperplasia, which enhances the deposition of RF or microwave energy in target tissue. It is a further object of the current invention to provide an improvement to said method which selectively enhances energy deposit in target tissue compared to adjacent tissue.

SUMMARY OF THE INVENTION

The present invention enhances the deposition of microwave energy in target tissue by means of injecting into the target tissue a biocompatible fluid which has high RF or microwave absorption characteristics as appropriate to the particular frequency being used. Preferably the frequency chosen has relatively low absorption in uninjected tissue. In particular, this invention enhances the deposition of RF and microwave energy in target tissue by means of injecting aqueous solutions of salts which create ionic solutions. This invention also enhances the deposit of RF and microwave energy in tissue by means of non-aqueous biocompatible organic fluids comprising either fluids alone or solutions of organic solids in compatible solvents which have absorption bands for microwave energy in wavelength ranges which are useful for microwave ablation of tissue. This invention will enhance absorption of microwave energy selectively by virtue of injecting the enhancing fluid only into the target tissue. It can also enhance selective absorption of microwave energy by using compounds which perfuse target tissue selectively compared to adjacent tissue.

DETAILED DESCRIPTION OF THE INVENTION

Figure 1A:
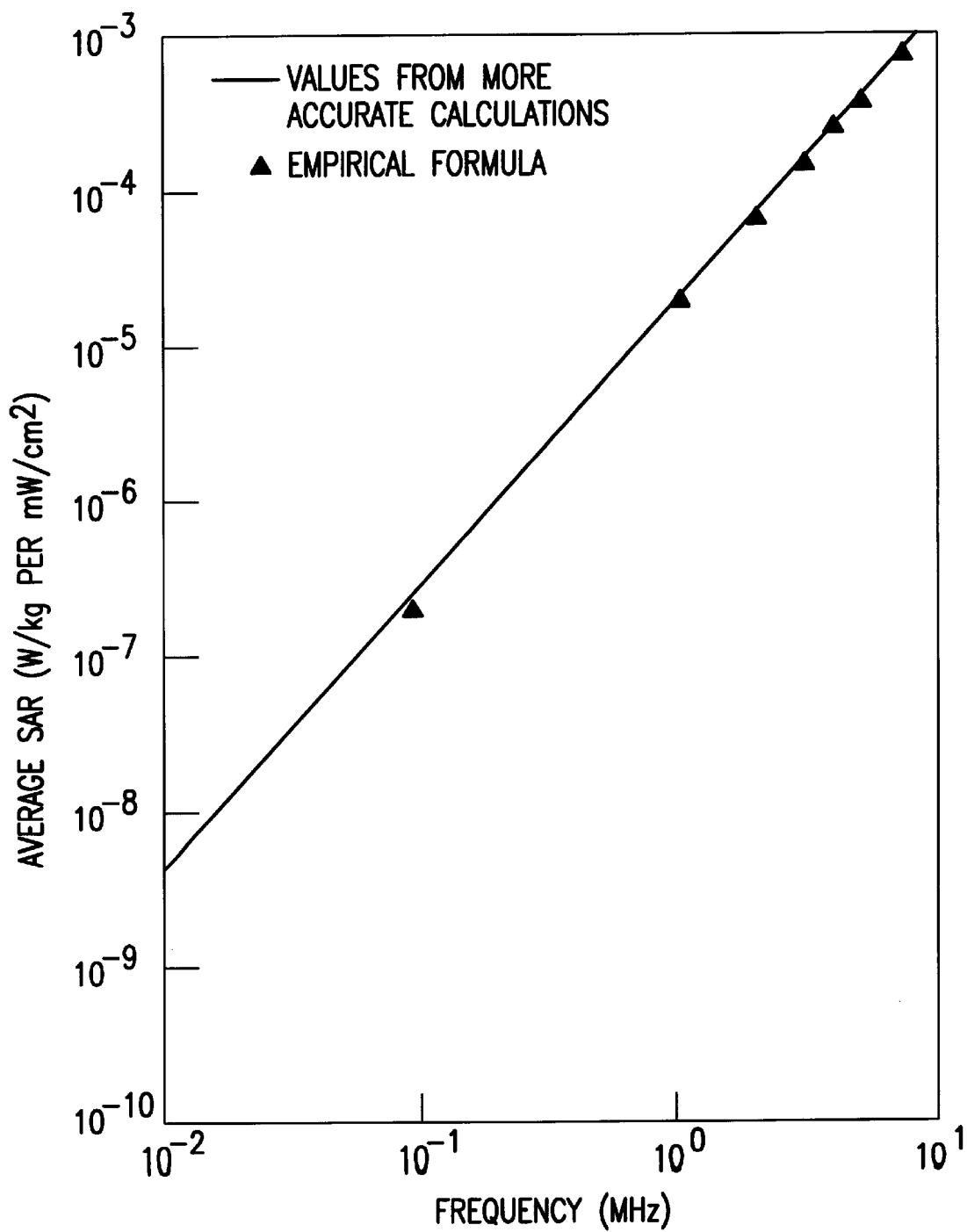
FIG. 1a shows the approximate absorption characteristics of human tissue for RF up to 10 MHz.

In the kHz range of frequencies, FIG. 1a shows that absorption of radiated RF energy in tissue is very low. It is known that in sufficient concentrations, however, dissolved salts of alkali metals and, among others, Fe, Mg, and Cr, absorb radiation in such a way as to cause enhanced heating of the solution. Various mechanisms, including pure resistive heating and ion cyclotron resonance in the Earth's magnetic field, can combine to provide significant RF absorption in such ionic solutions.

Many of such salts are biocompatible in solution in sufficient concentrations to provide enhanced deposit of RF energy. In particular, saline is a commonly used biocompatible ionic solution. Injected saline, for example, will enhance absorption of RF or microwave energy at some frequencies without itself damaging adjacent tissue.

In addition, it is known that most non-ionic organic compounds absorb radiation at various frequencies through various mechanisms, including polarization and dipole interactions. Most organic compounds of any complexity also have vibration and rotation absorption bands. Thus many organic fluids and organic solids which can be dissolved in fluids have RF and microwave absorption bands throughout the spectrum of interest. Of these many also are biocompatible. Examples are hypertonic glucose, hypertonic manitol, and other sugars. Some of these are liquids, others can be used in aqueous solution, and still others can be used in non-aqueous solutions.

Figure 1B:
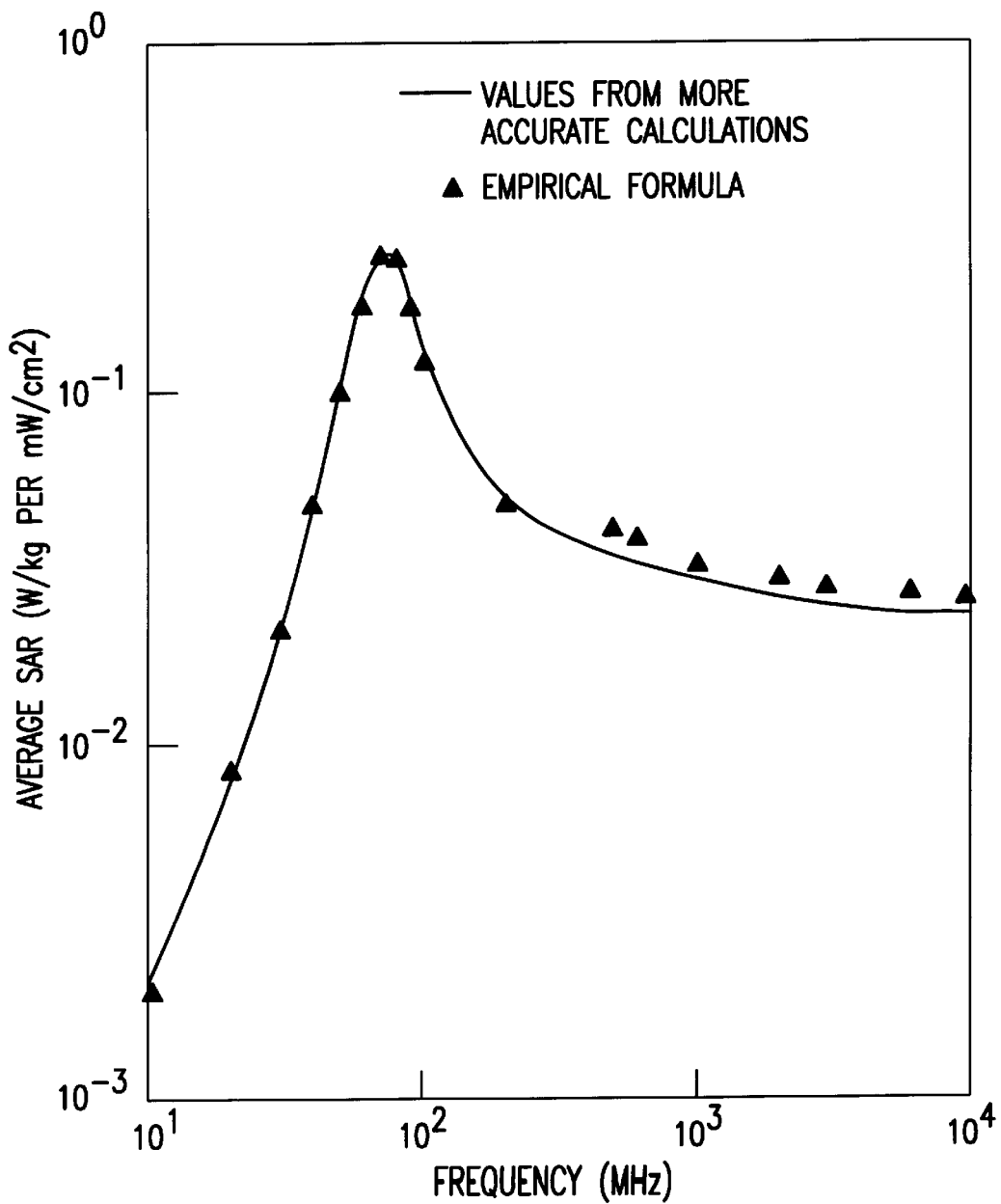
FIG. 1b shows the approximate absorption characteristics of human tissue for RF above 10 MHz and microwave radiation up to 10,000 MHz.

The method entails first selecting a combination of frequency of RF or microwave radiation which can be conveniently delivered to the body and an injectable biocompatible solution either of the ionic or organic type which has an absorption peak at the selected frequency. FIG. 1b shows that generalized human tissue has an absorption peak between about 80 MHz and 120 MHz. The preferred embodiment would be to select frequencies either well above or well below that peak in frequency regions for which absorption in human tissue is not too high in order to minimize collateral damage to non-targeted tissue. Preferably either the frequency of the RF or microwave signal is chosen to match the absorption band of a preselected enhancing substance or the substance is chosen so that its relevant absorption band matches the preselected frequency of absorption.

Figure 2:
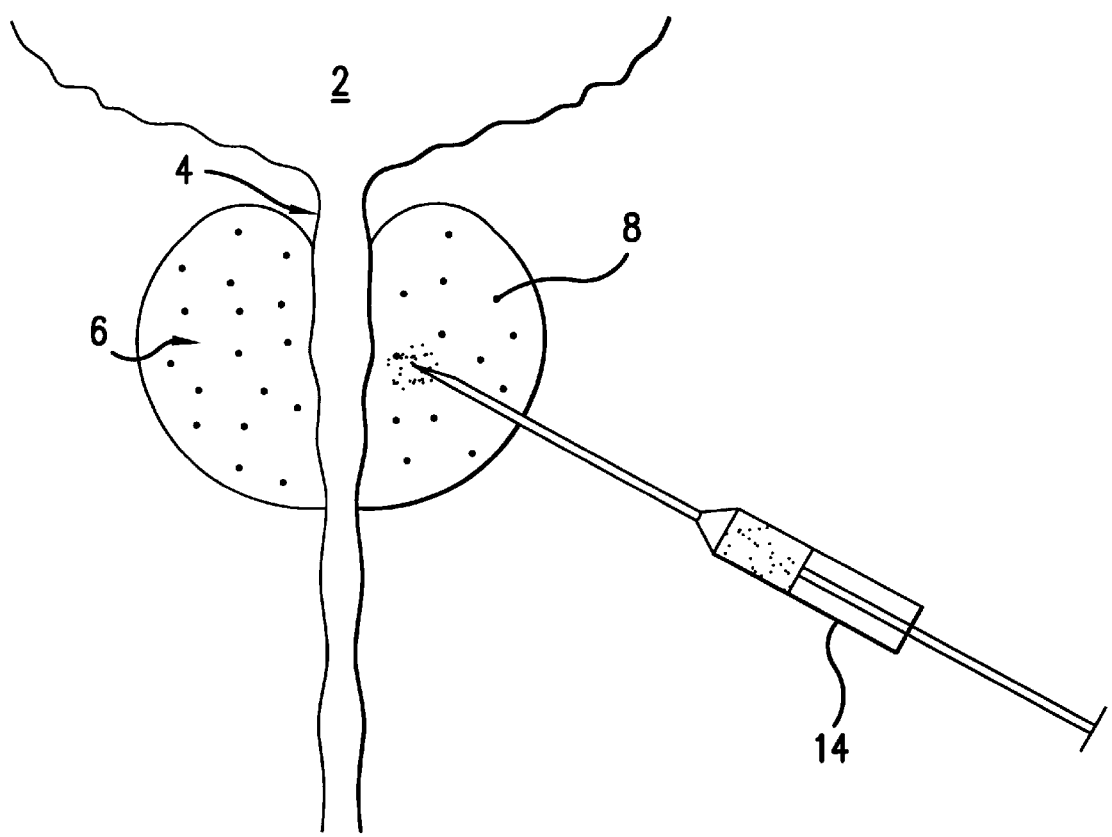
FIG. 2 shows the injection of enhancing fluid into target tissue.
Figure 3:
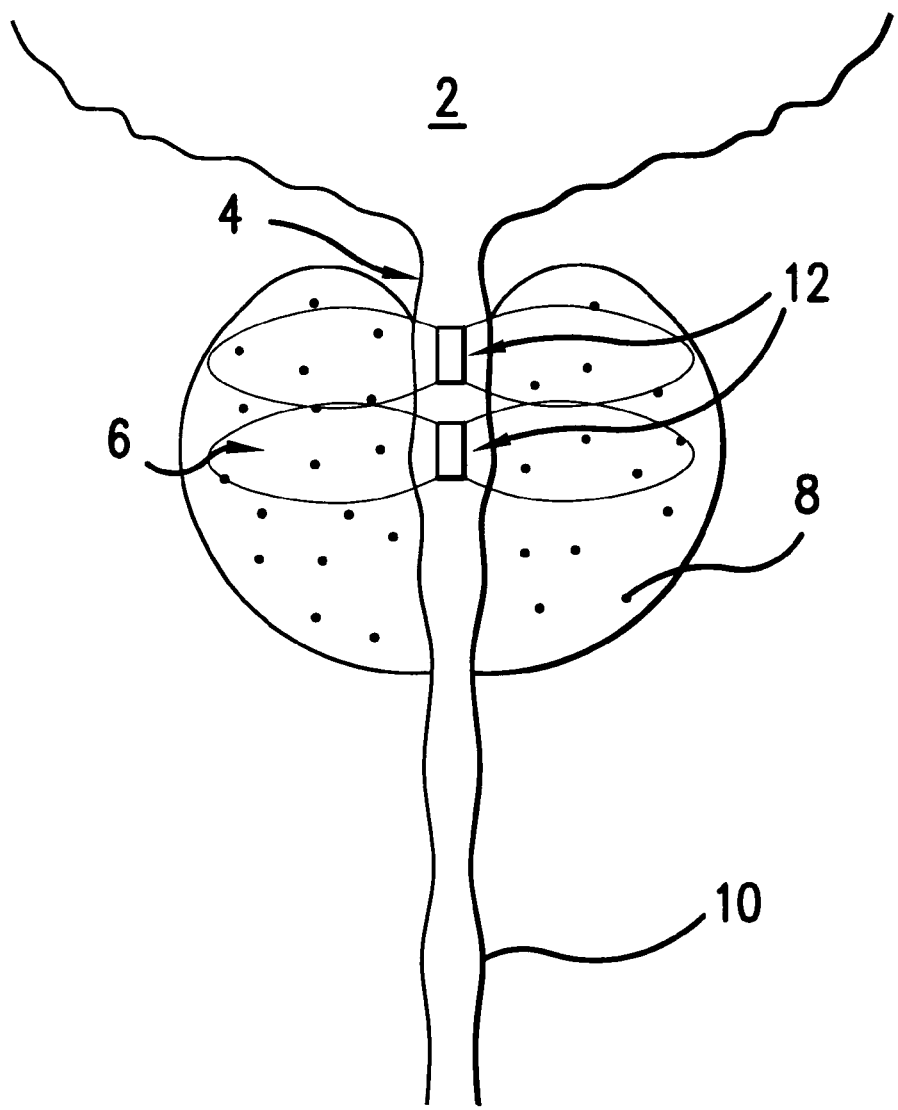
FIG. 3 shows an antenna radiating energy into the target tissue, which selectively absorbs it.

The procedure is for the physician to locate the target tissue within the prostate or other body part which is to be treated. The physician then injects the solution into the target tissue as shown in FIG. 2. Finally, an antenna is placed adjacent to the tissue, in the manner of the Urologix device referred to above, in the manner of the Sievert, et al. device, or in some other way, and radiation of the selected frequency is applied. See FIG. 3. After sufficient deposition of energy, treatment is discontinued, tissue necrosis takes place, and eventually the desired ablation is obtained.

What is claimed is:

1. A process for tissue ablation comprising the steps of
   perfusing into a target tissue volume a biocompatible fluid having at least one radio-frequency or microwave absorption frequency band;
   depositing radio-frequency or microwave energy in said target tissue volume by irradiating said target tissue volume with radio-frequency or microwave energy tuned to said at least one radio-frequency or microwave absorption frequency band, said biocompatible fluid thereby enhancing deposition of said radio-frequency or microwave energy in said target tissue volume relative to tissue adjacent to the target tissue volume.

2. The process of claim 1 in which the biocompatible fluid is an organic fluid.

3. The process of claim 1 in which the biocompatible fluid comprises an aqueous solution of an ionizing salt.

4. The process of claim 2 in which the organic fluid is a solution of an organic solid with at least one radio-frequency or microwave absorption frequency band.

5. A process for causing resorption of target tissue in a living human or animal by depositing radio-frequency or microwave energy in said target tissue, thereby raising the temperature of the target tissue sufficiently to cause necrosis and consequent resorption of said target tissue, said process comprising at least the steps of:
   selecting a radio-frequency or microwave energy source with a selected frequency;
   selecting a biocompatible fluid with an absorption frequency band for radio-frequency or microwave energy encompassing the selected frequency of the radio-frequency or microwave energy source;
   perfusing the target tissue with said biocompatible fluid prior to irradiating the target tissue with the radio-frequency or microwave energy;
   approximating the radio-frequency or microwave energy source to the target tissue;
   causing the radio-frequency or microwave energy source to emit energy in such a pattern as to irradiate the target tissue, thereby depositing at least a portion of said energy in the target tissue; and continuing said emitting until the target tissue temperature is raised sufficiently to bring about necrosis and consequent resorption;

whereby energy deposition is enhanced in the target tissue volume compared to energy deposition in tissue adjacent to the target tissue volume so that absorption of the radio-frequency or microwave energy is selectively enhanced in the target tissue volume compared to absorption in tissue adjacent to the target tissue volume.

6. The process of claim 5 wherein the biocompatible fluid comprises an aqueous solution of an ionizing salt.

7. The process of claim 6 wherein the anion of the ionizing salt is selected from the group consisting of halide, nitrate, nitrite, acetate, bicarbonate, and phosphate and the cation of the ionized salt is selected from the group consisting of alkali metal ions and alkaline earth metal ions.

8. The process of claim 6 wherein the anion of the ionized salt is a halide and the cation of the ionized salt is selected from the group consisting of alkali metal ions and alkaline earth metal ions.

9. The process of claim 6 wherein the cation of the ionizing salt is selected from the group comprising iron, chromium, and magnesium.

10. The process of claim 5 wherein the biocompatible fluid comprises an organic fluid.

11. The process of claim 10 wherein the organic fluid comprises a solution of an organic solid with a radio-frequency or a microwave absorption frequency band at the selected frequency.

12. The process of claim 5 in which the selected frequency is chosen to be above or below the peak frequency for absorption of electromagnetic energy in human tissue.

13. A process for causing resorption of target tissue in a living human or animal by depositing radio-frequency or microwave energy in said target tissue, thereby raising the temperature of the target tissue sufficiently to cause necrosis and consequent resorption of said target tissue, said process comprising at least the steps of:

selecting a biocompatible fluid with at least one absorption frequency band for radio-frequency or microwave energy;

selecting a radio-frequency or microwave energy source with a frequency encompassed by the at least one absorption frequency band of the biocompatible fluid;

perfusing a target tissue volume with said biocompatible fluid prior to irradiating the target tissue with radio-frequency or microwave energy;

approximating the radio-frequency or microwave energy source to the target tissue volume;

causing the radio-frequency or microwave energy source to emit energy in such a manner as to irradiate at least the target tissue volume, thereby depositing at least a portion of said energy in the target tissue; and continuing said emitting until the target tissue volume temperature is raised sufficiently to bring about necrosis and consequent resorption;

whereby energy deposition is enhanced in the target tissue volume relative to energy deposition in tissue adjacent to the target tissue volume so that absorption of the radio-frequency or microwave energy is selectively enhanced in the target tissue volume compared to absorption in tissue adjacent to the target tissue volume.

14. The improvement of claim 13 wherein the biocompatible fluid comprises an aqueous solution of an ionizing salt.

15. The improvement of claim 14 wherein the anion of the ionizing salt is selected from the group consisting of halide, nitrate, nitrite, acetate, bicarbonate, and phosphate and the cation of the ionized salt is selected from the group consisting of alkali metal ions and alkaline earth metal ions.

16. The improvement of claim 14 wherein the anion of the ionized salt is a halide and the cation of the ionized salt is selected from the group consisting of alkali metal ions and alkaline earth metal ions.

17. The improvement of claim 14 wherein the cation of the ionizing salt is selected from the group comprising iron, chromium, and magnesium.

18. The improvement of claim 13 wherein the biocompatible fluid comprises an organic fluid.

19. The improvement of claim 13 wherein the organic fluid comprises a solution of an organic solid with a radio-frequency or a microwave absorption frequency band.

20. The improvement of claim 13 in which the biocompatible fluid is selected so that the at least one absorption frequency band is above or below the peak frequency for absorption of electromagnetic energy in human tissue.

\* \* \* \* \*